US012385032B2

(12) United States Patent
Yang et al.

(10) Patent No.: US 12,385,032 B2
(45) Date of Patent: Aug. 12, 2025

(54) BEAUVERIA BASSIANA STRAIN WITH HIGH ULTRAVIOLET RADIATION RESISTANCE AS WELL AS DIRECTIONAL MUTAGENESIS METHOD THEREFOR AND USE THEREOF

(71) Applicant: ZHEJIANG TIDE CROPSCIENCE CO., LTD., Zhejiang (CN)

(72) Inventors: Zhengyu Yang, Zhejiang (CN); Laifu Wang, Zhejiang (CN); Peice Chen, Zhejiang (CN)

(73) Assignee: ZHEJIANG TIDE CROPSCIENCE CO., LTD., Zhejiang (CN)

( * ) Notice: Subject to any disclaimer, the term of this patent is extended or adjusted under 35 U.S.C. 154(b) by 0 days.

(21) Appl. No.: 18/800,329

(22) Filed: Aug. 12, 2024

(65) Prior Publication Data

US 2024/0392281 A1 Nov. 28, 2024

Related U.S. Application Data

(63) Continuation of application No. PCT/CN2023/089172, filed on Apr. 19, 2023.

(30) Foreign Application Priority Data

Apr. 22, 2022 (CN) ........................ 202210427183.X

(51) Int. Cl.

| | |
|---|---|
| ***C12N 15/01*** | (2006.01) |
| ***A01N 63/30*** | (2020.01) |
| ***A01P 7/04*** | (2006.01) |
| ***C12N 1/14*** | (2006.01) |
| ***C12N 13/00*** | (2006.01) |
| ***C12R 1/645*** | (2006.01) |

(52) U.S. Cl.

CPC ............. *C12N 15/01* (2013.01); *A01N 63/30* (2020.01); *A01P 7/04* (2021.08); *C12N 1/145* (2021.05); *C12N 13/00* (2013.01); *C12R 2001/645* (2021.05)

(58) Field of Classification Search

CPC ........ C12N 15/01; C12N 1/145; C12N 13/00; C12N 1/14; A01N 63/30; A01P 7/04; C12R 2001/645; Y02A 50/30

See application file for complete search history.

(56) References Cited

U.S. PATENT DOCUMENTS

2012/0263690 A1 10/2012 De Crecy

FOREIGN PATENT DOCUMENTS

| | | | |
|---|---|---|---|
| CN | 106434362 | A | 2/2017 |
| CN | 111424028 | A | 7/2020 |
| CN | 114292760 | A | 4/2022 |
| CN | 114317289 | A | 4/2022 |
| CN | 114317293 | A | 4/2022 |
| CN | 114317294 | A | 4/2022 |
| CN | 114736810 | A | 7/2022 |
| WO | 2020197163 | A1 | 10/2020 |

OTHER PUBLICATIONS

Fang, Weiguo, and Raymond J. St. Leger. "Enhanced UV resistance and improved killing of malaria mosquitoes by photolyase transgenic entomopathogenic fungi." (2012): e43069. (Year: 2012).*

International Search Report for corresponding International Patent Application No. PCT/CN2023/089172, mailed Jul. 21, 2023, 13 pages.

Shang, Y., et al., "Improving UV resistance and virulence of Beauveria bassiana by genetic engineering with an exogeneous tyrosinase gene", Journal of Invertebrate Pathology, 2012, vol. 109, pp. 105-109.

Golden, D., et al., "Role and mechanism of thiazole synthethase BbThl in tolerance to UV radiation damage in B. bassiana", Summary Collection of the 9th Member Congress and Annual Conference of Chongqing Microbiology Society, 2009, p. 71.

Supplementary European Search Report received in corresponding European patent application No. 23791263.9, dated Feb. 27, 2025, 7 pages.

Huang, Bao-Fu, et al., "Comparative Tolerances of Various Beauveria bassiana Isolates to UV-B Irradiation with a Description of a Modeling Method to Assess Lethal Dose", Mycopathologia, 2009, 168: 145-152.

Posadas, Julieta B., et al., "Natural Tolerance to UV-B and Assessment of Photoprotectants in Conidia of Six Native Isolates of Beauveria bassiana (Bals-Criv) Vuillemin", World Applied Sciences Journal, 2012, 20(7): 1024-1030.

Sutanto, Koko Dwi, et al., "Persistency of Indigenous and Exotic Entomopathogenic Fungi Isolates under Ultraviolet B (UV-B) Irradiation to Enhance Field Application Efficacy and Obtain Sustainable Control of the Red Palm Weevil", Insects, 2022, 13, 103, pp. 1-13.

Fernandes, Everton K.K., et al., "Variability in tolerance to UV-B radiation among *Beauveria* spp. isolates", Journal of Invertebrate Pathology, 2007, 96: 237-243.

(Continued)

*Primary Examiner* — Ekaterina Poliakova-Georgantas
*Assistant Examiner* — John Charles McKillop
(74) *Attorney, Agent, or Firm* — Cooper Legal Group, LLC

(57) ABSTRACT

The present application relates to the technical field of biology, in particular to a *Beauveria bassiana* strain with high ultraviolet radiation resistance as well as a directional mutagenesis method therefor and use thereof. The *Beauveria bassiana* strain with high ultraviolet radiation resistance of the present application has an accession number of CGMCC No.22466, and is deposited on Jul. 5, 2021. The strain is obtained by means of taking *Beauveria bassiana* wild strain CGMCC No.13566 as an original strain and performing multiple rounds of repeated stress and directional screening under simulated sunlight UVB sub-lethal radiation, and has high resistance to ultraviolet radiation. A fungal insecticide prepared by adopting the strain can be well applied to pest green prevention and control in all weather.

2 Claims, 3 Drawing Sheets

Specification includes a Sequence Listing.

(56) References Cited

OTHER PUBLICATIONS

Dias, Luciana P., et al., "The Xenon Test Chamber Q-SUN for testing realistic tolerances of fungi exposed to simulated full spectrum solar radiation", Fungal Biology, 2018, 122: 592-601.
Lee, Jin Yong, et al., "Beauveria bassiana for the simultaneous control of Aedes albopictus and Culex pipiens mosquito adults shows high conidia persistence and productivity", AMB Express, 2019, 9:206, pp. 1-9.
Office Action received in corresponding Japanese patent application No. 2024-577275, dated Jun. 4, 2025, 10 pages.

* cited by examiner

BEAUVERIA BASSIANA STRAIN WITH HIGH ULTRAVIOLET RADIATION RESISTANCE AS WELL AS DIRECTIONAL MUTAGENESIS METHOD THEREFOR AND USE THEREOF

CROSS-REFERENCE TO RELATED APPLICATIONS

This application is a continuation of PCT application no PCT/CN2023/089172, filed on Apr. 19, 2023, which claims the priority and benefit of Chinese patent application serial no. 202210427183.X, filed on Apr. 22, 2022. The entireties of PCT application no PCT/CN2023/089172 and Chinese patent application serial no. 202210427183.X are hereby incorporated by reference herein and made a part of this specification.

REFERENCE TO AN ELECTRONIC SEQUENCE LISTING

The contents of the electronic sequence listing (Sequence-Listing.xml; Size: 2,514 bytes; and Date of Creation: Aug. 12, 2024) is herein incorporated by reference.

REFERENCE TO A DEPOSIT OF BIOLOGICAL MATERIAL

The present disclosure contains references to biological material deposited under the terms of the Budapest Treaty on the International Recognition of the Deposit of Microorganisms for the Purposes of Patent Procedure at China General Microbiological Culture Collection Center, No. 3, Courtyard 1, Beichen West Road, Chaoyang District, Beijing, China.

TECHNICAL FIELD

The present application relates to a field of biotechnology, and, more particularly, to a *Beauveria bassiana* strain with high ultraviolet radiation resistance, directional mutagenesis and application thereof.

BACKGROUND ART

*Beauveria bassiana* is a broad spectrum insect pathogenic fungi, which generates a conidia by asexual reproduction. At present, formulated fungal insecticides prepared by the *Beauveria bassiana* conidia is used for pest biological prevention in world, in which the largest international biological pest prevention project is to use *Beauveria bassiana* to control pine caterpillars and corn borers in China, which realize a good and sustainable pest prevention effect.

However, the formulated *Beauveria bassiana* often suffers from a damage of sunshine ultraviolet radiation, thereby impairing stability and persistence of the pest prevention, which is significant in summer when there is sharply increased pest population and especially strong sunshine radiation. Therefore, the sunshine ultraviolet radiation limits all weather application of the fungal insecticides for green pest prevention. In particular, the sunshine ultraviolet radiation includes two harmful radiation components of UVB (290-320 nm) and UVA (320-400 nm), and fortunately, the shortest and most harmful UVC radiation (<290 nm) is totally filtered by atmosphere ozone layer before the sunshine reaches the surface of the earth. Therefore, UVB ultraviolet radiation damages the formed fungi cells most in the sunshine, and the impact of the relatively large wavelength UVA is relatively limited.

The *Beauveria bassiana* has one or two photolyases. Generally, the mechanism of eukaryotic cell repairing DNA damage caused by the ultraviolet radiation mainly relies on light repairing effect of photolyase positioned in nucleus, and a large part of damaged cells restore vitality by the photolyase quickly repairing the DNA damage caused by the radiation under visible light. Therefore, an expression level of the photolyase gene largely determines the light repairing effect of the fungal cells for the DNA damage.

At present, there are two ways for improving the expression level of the photolyase in the fungal cells. A first way is using exogenous resistance molecular markers to screen high-expression target gene, by which the screened resisting ultraviolet strain inevitably carries exogenous resistance genes and belongs to a transgene strain, so there is a hidden risk in terms of ecology safety. A second way is to select a strain with high ultraviolet resistance by directional mutagenesis and screening without using any exogenous molecule marking, in which, however, the existing selected *Beauveria bassiana* has limited resistant for the ultraviolet radiation, and is difficult to be well applied to the green pest prevention and control in all weather.

SUMMARY

For the purpose of solving a problem of poor ultraviolet radiation resistance in existing fungal insecticide, a *Beauveria bassiana* highly expressing photolyase gene is disclosed in the present application, the strain possesses relatively strong resisting ultraviolet radiation, and the fungal insecticides prepared thereby can be well applied to green pest prevention and control in all weather.

In the first aspect, the present application provides a *Beauveria bassiana* strain with high ultraviolet radiation resistance, which has an accession number of CGMCC No. 22466, and a deposit date of Jul. 5, 2021.

The *Beauveria bassiana* strain with high ultraviolet radiation resistance of the present application is disclosed, the conidia thereof for resistance of UVB radiation has been improved 53% than original strain, an expression level of key photolyase gene for repairing DNA damage is upregulated by 98 times, other traits related to biological control potential is completely identical to the original strain, and there is no exogenous resistance molecular marker having ecology safety hidden peril, which can be a generation strain of the fungal insecticides with high ultraviolet resistance, and has an important application value.

Preferably, a corrected mortality of the *Beauveria bassiana* strain with high ultraviolet radiation resistance infecting by penetrating through a body wall is ≥50% in sixth day, and ≥60% in seventh day.

preferably, an insect attachment rate of the *Beauveria bassiana* strain with high ultraviolet radiation resistance ranges in 92.5-110.3%.

In the second aspect, a directional mutagenesis method of the *Beauveria bassiana* strain with high ultraviolet radiation resistance of the present application is disclosed, the *Beauveria bassiana* strain with high ultraviolet radiation resistance is obtained by means of taking the *Beauveria bassiana* wild strain of CGMCC No. 13566 as an original strain, and performing multiple rounds of repeated stress and directional screening under simulated sunlight UVB sub-lethal radiation.

Preferably, the directional mutagenesis method comprising following steps:

- step 1: adopting the *Beauveria bassiana* wild strain CGMCC No. 13566 as the original strain, preparing a spore suspension of conidia thereof;
- step 2: uniformly coating the spore suspension on a culture medium plate, radiating the plate by UVB sub-lethal dose in a sunshine simulation radiation box;
- step 3: Cultivating radiated individual existing spore to grow a colony, selecting thriving colony and transferring to a sporulation culture plate, cultivating until the colony is fully sporulated, wherein the conidia is used for testing UVB resistance, screening the colony that UVB resistance thereof is further significantly increased in a previous round best colony, and simultaneously testing whether there is a significant change of growth sporulation and toxicity trait; and
- step 4: repeating the mutagenesis and screening steps 1, 2 and 3 until the UVB resistance of the previous round best target colony is no longer improved in next round, and selecting the strain having great UVB resistance in last round of mutagenesis screening as the *Beauveria bassiana* strain with high ultraviolet radiation resistance.

The *Beauveria bassiana* disclosed by the present application is token as an original strain, an obtaining source of the material is wild, and the *Beauveria bassiana* is performed multiple rounds of repeated stress and directional screening under simulated sunlight UVB sub-lethal radiation, which is more convenience to operate when it is compared with genetic manipulation or gene editing, such that the screened strain is a molecular directed improvement strain without any exogenous gene, and should be regard as a non transgene strain, and the formed productions thereof are not necessary to pass an extra, rigorous, cumbersome and expensive environment safety evaluation.

Preferably, the conidia in step 1 is dispersed to the spore suspension by a sterile water comprising 0.01-0.06% Tween-80.

By adopting above solution, the Tween-80 is a hydrophilic surfactant, can strongly damage cell membrane and occur to an irritability, the low dose Tween-80 of the present application can increase a permeability of the conidia membrane, so as to facilitate the directional mutagenesis of the spore, and can increase a breeding efficient of the *Beauveria bassiana* to a certain extent.

Preferably, the culture medium in step 2 is a sabouraudmedium.

By adopting above solution, the formula of the sabouraudmedium includes yeast extract powder, glucose, peptone, and agar, which is a medium generally used for fungal isolating culture. The sabouraudmedium of the present application is enough to supply a basic nutritional composition for the growth of the *Beauveria bassiana*, this is a preference based on the strain of the present application needed to be screened with a strong environment durability, which needs not to additionally prepare an exclusive culture medium, can reduce a breeding cost to a certain extent, and can effectively screen a mutation strain of great performance.

Preferably, the UVB sub-lethal dose in step 2 ranges in 0.35-0.4 $J/cm^2$.

By adopting above solution, the above sub-lethal dose can lead about 95% of the conidia to death, and a few surviving conidia possesses relatively strong resisting ultraviolet strain, thereby effectively improving breeding efficiency of the *Beauveria bassiana*.

Preferably, the radiated culture medium in step 3 is cultivated at 22-28° C. and photoperiod of (10-14):(10-14).

The radiation temperature and the photoperiod are key reasons for affecting mutation of the strain, the mutagenesis strain cultivated by above temperature and photoperiod is beneficial for screening the *Beauveria bassiana* strain with high ultraviolet radiation resistance of the present application adapting field application environment.

Preferably, the present application is based on above direct mutagenesis method, comprising obtaining the conidia of the colony screened in step 4, soaking the conidia in a aqueous trehalose-ethanol solution, uniformly coating the spore suspension on the culture medium, radiating the plate by the UVB sub-lethal dose in the sunshine simulation radiation box, cultivating a radiated alive spore to grow the colony, selecting a thriving colony and transferring to a sporulation culture plate until the colony is fully sporulated, wherein the conidia is used for testing the UVB resistance, screening the colony that UVB resistance thereof is further significantly increased in a previous round best colony, and simultaneously testing whether there is a significant change of growth sporulation and toxicity trait, and selecting the strain having great UVB resistance screened in last round of mutagenesis screening as the *Beauveria bassiana* strain with high ultraviolet radiation resistance;

By adopting above solution, the spore of the strain selected in step 4 is soaked by the aqueous threhalose-ethanol solution, in which the threhalose is used in extracellular, however, the threhalose can not only effectively improve the resisting ultraviolet radiation of the soaked spore, but also facilitates a rapid germination and a stability growth of the spore under the UVB sub-lethal dose, and further facilitate a higher expression level of the key photolyase gene repairing the DNA damage for the grown strain, which may be due to a great protection effect of the threhalose attaching the strain in extracellular, such that the photolyase gene can be stably expressed in intracellular, and the ethanol thereof can increase a permeability of the cell wall and membrane of the spore, and the nutrients of the culture medium can rapidly enter in to the cell to supply enough nutrients for the expression of the photolyase gene.

In the third aspect, the present application discloses an application of the *Beauveria bassiana* strain with high ultraviolet radiation resistance in preparing a fungal insecticide, and the prepared fungal insecticide overcomes a commonly key technical bottleneck of poor filed stability of the fungal insecticide, and has a great field stability, sustainability and pest prevention effects.

DETAILED DESCRIPTION

Figure 1:
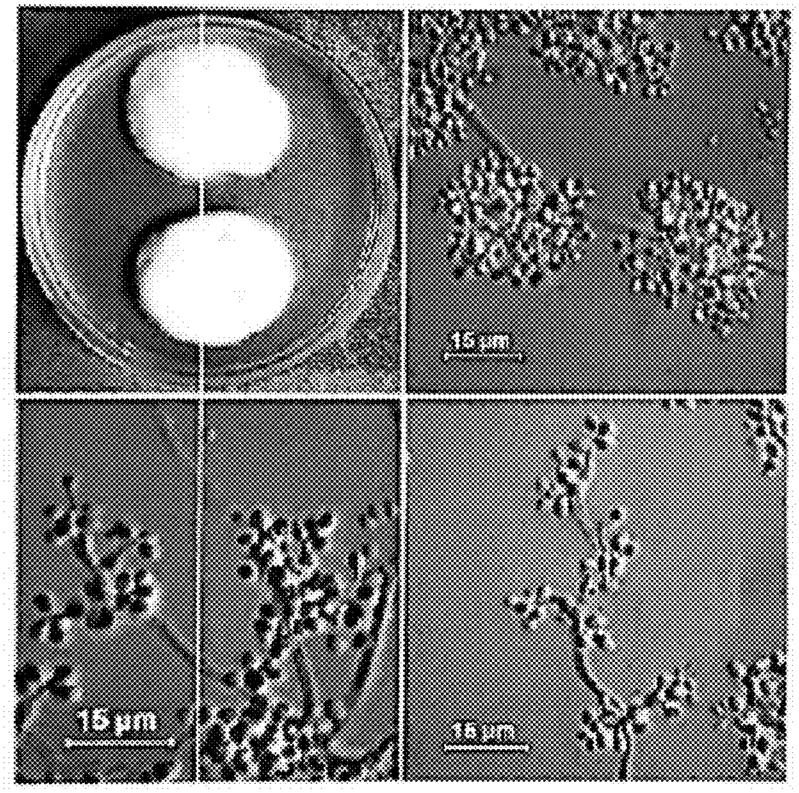
FIG. 1 is a colony morphology and a microscopic characteristic of resisting ultraviolet radiation mutagenesis strain of the present application.

The present application is further described below in detail below in combination with Drawings, Examples and Comparative Examples.

Sources of Raw Material

The raw materials of the present application were bought from market production, the specification of which is shown in Table 1,

TABLE 1 the sources of the raw material in the present application

| Raw material | Source/Performance |
|---|---|
| *Beauveria bassiana* (CGMCC No. 13566) | the source of strain: Microbial research isolation and cultivation at Zhejiang University, strain number: ZJU435 identification of Institute of Microbiology, Chinese Academy of Sciences (identification test 2019 May 22, detection operator: Zujin Sun; head of detection: Xingzhong Liu: Colony morphology, spore production structure, and conidia of the strain to be tested ZJU435 (China Microbial Strain Collection Center accession number CGMCC No. 13566) is same as the characteristics of *Beauveria bassiana* (Balsamo-Crivelli) Vuillemin. The spore production structure is curved as knee or zigzag shape, and has stem with a small dentate protrusions (conidiophore), the spores are spherical or nearly spherical, the diameter is 2-3 × 2-2.5 μm. ITS sequence (appendix) of the strain to be tested and the ITS sequence of 44 known insect pathogenic fungi are processed phylogenetic clustering analysis, which shows that the strain to be tested and known six *Beauveria bassiana* are cluster to one and bootstrap support rate of which is ultra-high. the present report identifies the strain to be tested to *Beauveria bassiana* according to a principle that one fungi has one name. |
| Sabouraudmedium (SDAY) | 4% glucose, 1% peptone, 1% yeast powder, and 1.5% agar powder |

Example 1

A directional mutagenesis of *Beauveria bassiana* strain with high ultraviolet radiation resistance includes following steps:

step 1: *Beauveria bassiana* CGMCC No. 13566 (simply named wild strain) was an original strain, and the conidia generated by being normally cultured on the sabouraudmedium (SDAY) plate was suspended in the sterile water including 0.02% Tween-80 (allowed to be fluctuated in range of 0.01-0.06%), which was prepared to the suspension of $10^7$ spores/mL;

step 2: the above 60 μL spore suspension was uniformly coated on the SDAY plate under sterile condition. After drying a few minutes in air (to dry the coated spore suspension), the plate was placed on sample stable (12 cm×16 cm) of sunshine ultraviolet radiation simulation box Bio-Sun++ UV Chamber (Vilber Lourmat, Marne-la-vallée, France), and was processed by UVB radiation via the sub-lethal dose of 0.38 J/$cm^2$ (allowed to be fluctuated in range of 0.35-0.4 J/$cm^2$), which leaded to death of about 95% of the spores;

step 3: the plate coated with the spores were immediately covered after the radiation, and cultured at temperature of 25° C. and photoperiod of 12:12 (allowed to be fluctuated in range of 22-28° C. and photoperiod of (10-14):(10-14)), until a few survival spores grows colonies, the thriving colonies were selected and transferred to a new SDAY plate medium until the colonies were fully sporulated, the obtained spores were used for UVB resistance testing, the colonies that UVB resistance thereof further significantly increased on a previous round best colony were screened, and whether there were significant changes of growth sporulation and toxicity trait was simultaneously tested; and step 4: mutagenesis and screening steps 1, 2 and 3 were repeated until the UVB resistance of the previous round best target colony was no longer improved in next round, and a strain having great UVB resistance in last round of mutagenesis and screening was selected as a *Beauveria bassiana* strain with high ultraviolet radiation resistance.

Biological Identification of the Mutated Strain (Colony Morphology, Microscopic Characteristics, and Gene Sequence Determination)

The above mutated *Beauveria bassiana* strain with high ultraviolet radiation resistance of the present application was sent to the institute of Microbiology, Chinese Academy of Sciences for biological identification and deposition on Jul. 5, 2021, having a strain number of TICZJU618 (China Microbial Strain Collection Center accession number CGMCC No. 22466), and it was identified that the strain was *Beauveria bassiana.*

Morphology and microscopic characteristics (referring to FIG. 1) of the colony were as follow.

The examined strain grew quickly on potato glucose medium, and reached a colony having a diameter of 30-35 cm under dark of 25° C. for 7 days, showing dense texture, flocculent appearance, white color, slight protrusion, light brown back of the colony, and no soluble pigment.

A specialization of conidiophore was not obvious, the shape of the sporulation cell was a flask, straight or curved, the length was 6.1-35.8 μm, the diameter was 1.5-2.5 μm, the neck was slender, the top was extended as zigzag shape, the width was less than 1 μm, which was grew singly or clustered; and the conidia was oval and nearly spherical, and colourless, the wall thereof was smooth, the diameter was 1.5-3.0 μm, and there is no sexual sporulation structure.

The result of rRNA gene sequence determination was as follows:

Comprising 18SrRNA segment, ITS1, 5.8rRNA, complete sequence of ITS2 and sequence segment of 28S region, in which the sequences was as shown in SEQ ID NO. 1.

The Repeatability of the Directional Mutagenesis Method

Three testers processed the tests according to the directional mutagenesis of Example 1, and processed the biological identification, respectively. The colony morphology, the microscopic characteristics, and the conservative gene sequences of the mutagenesis strain obtained by the three testers are identical, which means that the directional mutagenesis method of the present application has a repeatability, and can stably induce and breed the mutagenesis strain of the present application.

Performance Comparison Test Between the Mutagenesis Strain and Wide Strain

The mutagenesis strain having great UVB resistance in the last round of the mutagenesis strain and the screening processed following comparing experience with the wild strain.

1. UVB Resistance Test

The test method was as follows: the 60 L conidia suspension ($10^7$ spores/mL) was uniformly coated on the SDAY plate (diameter was 9 cm), provided on the sample stage of above sunshine ultraviolet radiation simulation box and processed the UVB radiation of gradient doses (0.1~0.5 J/$cm^2$), the radiated plate was covered and cultured at 25° C. and photoperiod of 12:12, and the unirradiated plate was regarded as a control. During culturing period, total number of spore count and germinated spore count of three views are detected under a microscope every two hours from forth hour, the spore surviving index was calculated (dividing percentage by 100), then the fitting of a model of the surviving index of the gradient doses was analyzed, and the sub-lethal dose $LD_{50}$ of the UVB was obtained. The experiment of each dose was set three independent repetitions.

The detection results were shown in FIGS. A and B.

2. Expression Level Test of Key Photolyase Gene

The test method was as follows: the 100 L conidia suspension of the wild strain and mutagenesis strain were uniformly coated on the SDAY plate attaching with a glass paper, the culture was obtained at 25° C. and photoperiod of 12:12 for three days, which was ground by liquid nitrogen and extracted the total RNA of the strains via the RNAiso Plus Kit (TaKaRa Company in Dalian, China), and reversely transcribed RNA into cDNA via PrimeScript RT reagent Kit (TaKaRa). The obtained cDNA was regarded as a template, and processed real time quantitative PCR analysis under SYBR Premix Ex Taq enzyme (TaKaRa), and the expression level of photolyase gene phr2 in each stain was tested, in which β-actin gen was regarded as an inner reference. The expression level of the target gene in the mutagenesis strain relative to the wild strain was calculated by the $2^{-\Delta\Delta CT}$ method. Three cDNA independent samples of each strain were repeatedly measured.

Figure 2:
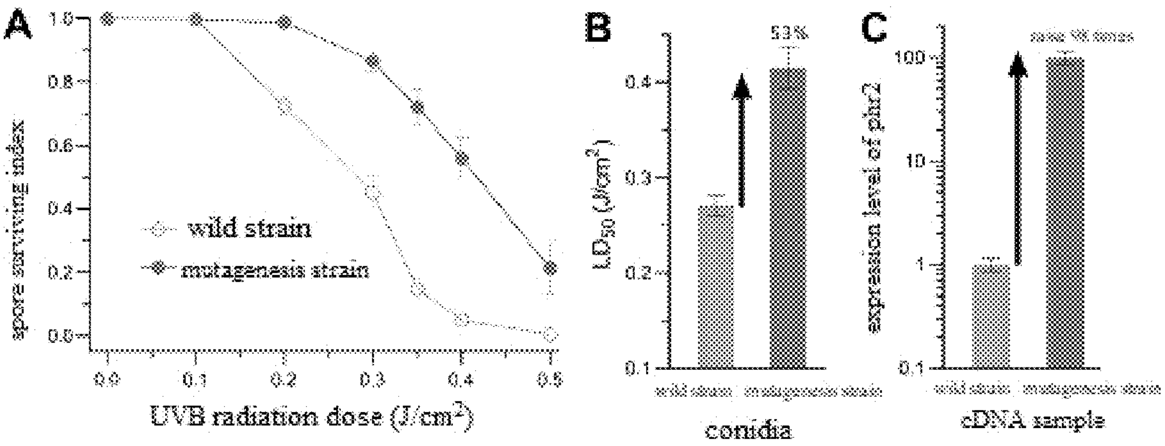
FIG. 2 is a UVB resistance schematic comparison view between the *Beauveria bassiana* original strain and the resisting ultraviolet radiation mutation strain of the present application; in particular, (A) is an existing trend of a conidia with changes of UVB radiation dose, (B) is a required UVB radiation $LD_{50}$ based on a fitting curve of radiation dose—spore survival index to calculate spore inactivation of 50%, (C) is an expression level of photolyase gene phr2 in mutagenesis strain relative to wild strain; error line; and standard deviation (SD) of three repeated experiment average value.

The detection result was shown in FIG. 2C.

3. The Toxicity of Normal Cuticle Infection and Cuticle-Bypassing Infection

The test method was as follows: the model insect fifth instar larvae of the wax moth was regarded as a test insect, and each group of 35 heads was soaked into 40 mL spore suspension ($10^7$ spore/mL) for 10 seconds, which was used as an inoculating way of the normal cuticle infection. Each head of larvae of each group was injected 5 μL spore suspension ($10^5$ spore/mL) to hemocoel via a microsyringe, which was used as an inoculating way of the cuticle-bypassing infection. Then, each group of the larvae was transfer into transparent plastic box, set at 25° C. and photoperiod of 12:12, and observed and recorded number of dead and surviving insects every day until all larvae were death. An equal amount of 0.02% Tween-80 solution immersion or injection treatment was used as the control, calculated the corrected mortality day by day. Every treatment was repeated three times. The obtained time-mortality curves were analyzed by the fitting of a model to calculate time $LT_{50}$ value of 50% death of test insects in different inoculating ways of each strain.

Figure 3:
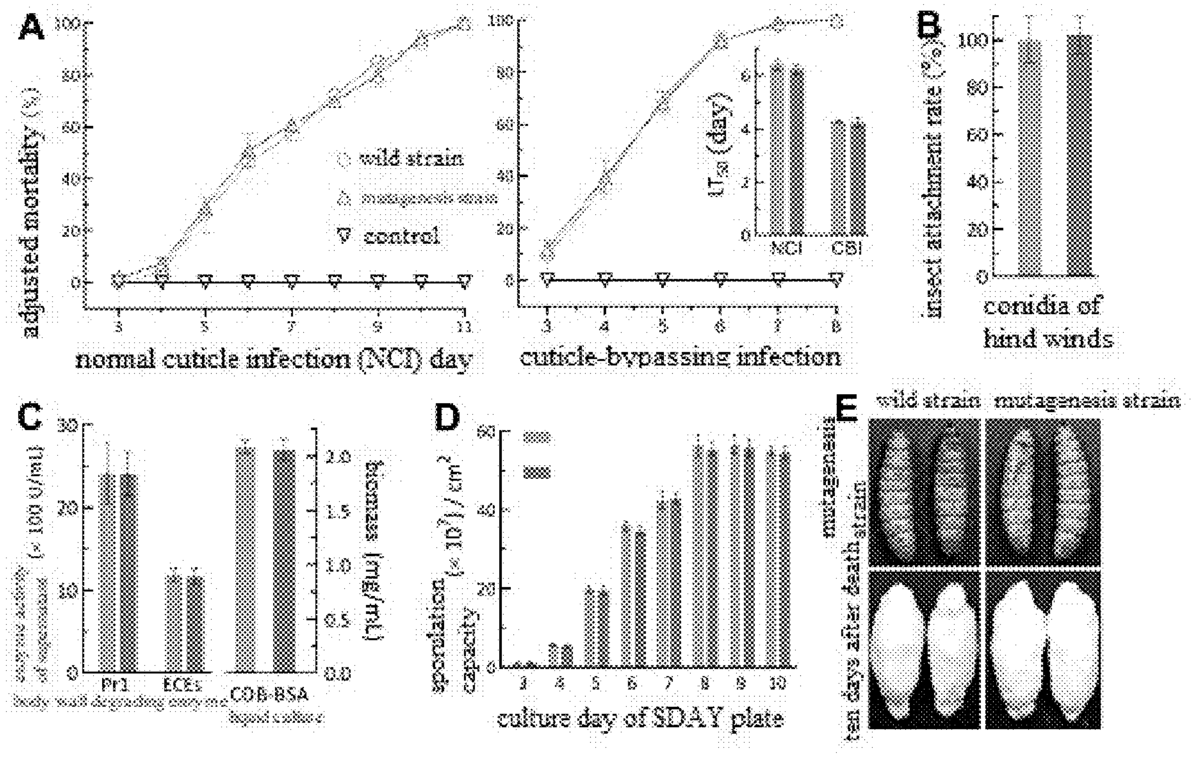
FIG. 3 is a schematic comparison view of toxicity and sporulation traits between the *Beauveria bassiana* original strain and the resisting ultraviolet radiation mutagenesis strain; in particular, (A) is a corrected mortality tendency and required time $LT_{50}$ of 50% death of fifth instar larvae of the wax moth after spore suspension ($10^7$ spores/mL) infects 500 spores by normal cuticle infection (NCI) and cuticle-bypassing infection (CBI). (B) is an attachment rate comparison of the required conidia on hind wings body wall of locusts. (C) is comparison between the biomass of the CDB-BSA culture medium and a total enzyme activity of extracellular enzyme (ECEs) required for that NCI successfully penetrated the insect body wall and body wall degrading enzymes, such as Prl family protein enzyme and so on, in supernatant of the culture medium. (D) is a sporulation capacity of the conidia during a period of normal culture after the spore suspension is coated on sabouraudmedium (SDAY). (D) is a surface growth comparison between fresh insect carcasses and 10 days after death after the giant wax moth larvae died of illness, which shows that the growth sporulation level of the mutagenesis strain in insect carcasses is totally same as the wild strain; error line; and standard deviation (SD) of three repeated experiment average value, it should be noticed that there is no significantly different between the mutagenesis strain and the wild strain on all test performance.

The detection result was shown in FIG. 3A.

4. The Test of Ability of Conidia to Attach to Surface of Insect Body Determining Success Rate of Normal Cuticle Infection The test method was as follows: the hind wings of Locusta migratoria manilensis were token, soaked in 37% $H_2O_2$ solution for 5 minutes to disinfect, and washed three times by the sterile water and attached on 0.7% water agar plate. The spore suspension ($10^7$ spore/mL) 5 μL was equally dripped in the center of the surface of the hind wings, and coated evenly by the transferring loop. After culturing eight hours at 25° C., the hind wings were immediately token and set on the glass slide, observed three views under the microscope, and calculated the number of conidia in each view. The observed hind wings were washed in sterile water for 30 seconds to remove the spore unattaching on the body surface of the hind wings, and observed three views of wing surface under the microscope and calculated the remaining spore count. The percentage of the spore count after washing compared to the spore count on the wing surface before washing was calculated to acquire an attaching rate of the conidia on the surface of the hind wings of the locusts.

The detection result was show in FIG. 3B.

5. Test of Total Enzyme Activity of Major Insect Body Wall Degrading Enzyme

The test method was as follows: the conidia suspension of each strain was inoculated in a basic culturing liquid CDB including 0.3% bovine serum albumin (BSA) as a unique nitrogen source (3% sucrose, 0.3% $NaNO_3$, 0.1% $K_2HPO_4$, 0.05% KCl, 0.05% $MgSO_4$ and 0.001% $FeSO_4$), in which the final concentration was $10^4$ spore/mL. The hypha was collected after shaking (150 r/min) and culturing at 25° C. for three days, and biomass was tested after drying at 75° C.; the supernatant of the culture liquid was centrifuged at 13500×g under 4° C. for 2 min, and collected as a crude extract to test the total enzyme activity of secreted extracellular enzymes (protein enzymes, chitinases, lipases, and so on, which were abbreviated as ECEs) and Pr1 family protein enzymes. The test of the total enzyme activity of the extracellular enzyme: 100 μL azoprotein (dissolved in 50 mM Tris-HCl, pH 8.0) solution with the concentration of 5 mg/mL was token, and fully mixed with 100 μL protein crude extract denatured through boiling water bath at 15 minutes (control group) or undenatured protein crude extract (experimental group), incubated without sunshine at 37° C. for an hour, and end reaction by adding 400 μL 10% (w/v) trichloroacetic acid. After centrifuging at 12,000×g for 5 minutes, the supernatant was absorbed and transferred to a new centrifuge tube, fully mixed with 700 μL NaOH with centration of 525 mM, and read absorbance value ($OD_{442}$) at 442 nm wavelength. The test of total enzyme activity of Pr1 protein enzyme: 100 μL protein crude extract denatured through boiling water bath (control) or undenatured protein crude extract was token and fully mixed with 50 μL reaction substrate with concentration of 1 mM [succinyl-(alanine) 2-proline-phenylalanine-p-nitroanilide] and 850 μL Tris-HCl buffer (15 mM, pH 8.5), and held at 28° C. for 1 hour; and 250 μL 30% (w/v) acetic acid was added to end the reaction. The reaction system was in ice bath for 15 minutes, centrifuged at 13000×g under 4° C. for 5 minutes, and the supernatant was token and read the absorbance value ($OD_{410}$) at 410 nm wavelength. The enzyme activity unit was defined as an incremental change of 0.01 in $OD_{442}$ or $OD_{410}$ reading during the reaction period, and total enzyme activity represented the number of extracellular enzyme activity units (U/mL) contained in the supernatant of each milliliter of the culture liquid.

The detection result was shown in FIG. 3C.

6. Test of Sporulation Level in Normal Growth

The test method was as follows: the test was processed by referring to spore count test method of SB/T 10315-1999.

The detection result was shown in FIG. 3D.

7. The Observation of Sporulation Level Grew on Surface of Insect Carcasses

The test method was observation.

The detection result was shown in FIG. 3E.

In summary, the *Beauveria bassiana* of the present application was obtained via repeated UVB sub-lethal dose radiation mutagenesis, in which the resistant of the conidia for the UVB radiation compared with the original strain improved 53% (FIG. 2B), the expression level of the photolyase gene phr2 repairing the DNA damage significantly raised 98 times (FIG. 2C), and there was no exogenous resistance molecular marker, so there was no ecology safety hidden peril.

Since the way of field sterilization using haemocoele injection of each insect body was time-consuming and laborious, it generally adopted the way of the normal cuticle infection, and the wild environment was uncontrollable. Therefore, the efficient of normal cuticle infection of the *Beauveria bassiana* was faster, and the attaching rate for the insect body was higher, such that the *Beauveria bassiana* better killed the insects. Referring to FIGS. 3A and 3B, the mortality of the *Beauveria bassiana* of the present Example by the normal cuticle infection was higher than the wild strain at three to seven days, in which the corrected mortality of the normal cuticle infection was 52.0% (the wild strain was 46.2%), and the corrected mortality of the normal cuticle infection was 61.3% (the wild strain was 57%), it could be seen that the efficient of the normal cuticle infection the mutagenesis strain was faster. In the aspect of the insect attachment rate, the insect attachment rate of the mutagenesis strain was 101.2% (ranged in 94.7 to 109.8% region after adding standard deviation), and the insect attachment rate of the wild strain was 99.0% (ranged in 90.3 to 110.0% region after adding standard deviation), which means that the attachment rate and the attachment stability of the conidia of the mutagenesis strain on the locust wings was higher than the wild strain.

Besides, the performance of the growth, the sporulation and the toxicity of the *Beauveria bassiana* of the present Example was same as the wild strain. (FIG. 3C-E).

Therefore, the *Beauveria bassiana* of present Example can be the generation strain of the resistant sunshine violet radiant fungal insecticide, increases the resistance of the fungal insecticide for the violet radiant and stability for the field pest prevention efficiency, and have a great normal cuticle infection and insect attachment rate, thereby having a great application value.

Example 2

The present Example was based on the method of Example 1, and adjusted the photoperiod of 12:12 to 10:14 to directly screen corresponding mutagenesis strain.

Example 3-4

The Example 3-4 was based on the method of Example 1, and adjusted sub-lethal dose 0.38 J/cm$^2$, in which the sub-lethal dose is 0.3 J/cm$^2$ in Example 3, and the sub-lethal dose is 0.45 J/cm$^2$ in Example 4, to directionally screen corresponding mutagenesis strain, Referring to the performance comparing experiment steps of the above Example 1, the performance of the wild strains and the mutagenesis strains screened in Examples 2-4 was tested, the detection results showed that colony morphology and microscopic characteristics of the mutagenesis strain screened in Examples 2-4 was similar to the mutagenesis strain screened in Example 1, and resistant for UVB radiant of conidia improved 45%, 46% and 49%, the expression levels of the photolyase gene phr2 repairing DNA damage raised 56 times, 67 times and 77 times, corrected mortality of normal cuticle infection in sixth day was 50.2%, 50.5% and 51.0%, the corrected mortality of the normal cuticle infection in seventh day was 60.0%, 60.2% and 60.6%, and insect attachment rate were 99.1% (ranged in region of 92.5 to 110.3% after adding standard deviation), 100.5% (ranged in region of 93.7-110.1% after adding standard deviation) and 100.7% (ranged in region of 94.1-110.0% after adding standard deviation). It can be seen that the mutagenesis strain in Example 1 have a greater resisting ultraviolet radiant effect, the greater normal cuticle infection and the greater attachment rate for the insect body. Therefore, the directional mutagenesis method of Example 1 is adopted as a further preference in the present application.

Example 5

The present Example further included step 5 based on the method of Example 1, specifically including the following steps:

Conidia of colony selected in step 4 was harvested, the conidia was soaked into the aqueous trehalose-ethanol solution at 10 to 15 min, in which the concentration of the threhalose was 0.3 to 0.6 g/L, and the volume concentration of the ethanol in ethanol solution was 5-10%. The treatment effect for the spores was similar in the above range, whereas the obtained mutagenesis strain grew poor beyond above range. In the present application, the conidia was soaked in the 0.5 g/L threhalose-8% ethanol solution at 10 minutes to prepare a spore suspension.

The above 60 μL spore suspension was uniformly coated on the SDAY plate, and dried in air after a few minutes (to dry the coated spore suspension). The plate was provided on the sample table (12 cm×16 cm) of sunshine violet radiant simulation box Bio-Sun++ UV Chamber (Vilber Lourmat, Marne-la-vallée, France), and processed UVB radiation by sub-lethal dose of 0.38 J/cm$^2$ (allowed to fluctuate in range of 0.35-0.4 J/cm$^2$);

The plate coated with the spore was immediately covered after radiation, cultured at temperature of 25° C. and photoperiod of 12:12 (allowed to fluctuate in range of 22-28° C. and photoperiod of (10-14):(10-14)) until the surviving spores grew colony, the thriving colony was transferred into a new SDAY plate to culture until the colony was fully sporulated, in which the spore was used for testing UVB resistance, the colony that UVB resistance thereof was further significantly increased on a previous round best colony was screened, and whether there was a significant change of growth sporulation and toxicity traits was simultaneously tested; and the mutagenesis strain having great UVB resistance in last round was selected as a *Beauveria bassiana* strain with high ultraviolet radiation resistance.

Referring to performance comparing experiment steps of the above Example 1, the performance of the wild strains and the mutagenesis strains screened in Examples 5 was tested, the detection results showed that the colony morphology and the microscopic characteristics of the mutagenesis strain screened in Examples 5 was similar to the mutagenesis strain screened in Example 1, and the resistant for UVB radiant of conidia improved 61% (Example 1 was 53%), the expression levels of the photolyase gene phr2 repairing DNA damage raised 112 times (Example 1 was 95 times), the corrected mortality of normal cuticle infection in sixth day was 54% (Example 1 was 52.0%), the corrected mortality of the normal cuticle infection in seventh day was 62.5% (Example 1 was 61.3%), and the insect attachment rate was 101.0% (ranged in region of 96.0-107.2% after adding standard deviation) (Example 1 was 101.2% (ranged in region of 94.7-109.8% after adding standard deviation)).

It can be seen that the mutagenesis strain was screened by the directional mutagenesis method in Example 1, soaked by the aqueous trehalose-ethanol solution and cultured to generate the spores, which can obtain the mutagenesis strain having greater resisting ultraviolet radiation effect, the normal cuticle infection efficiency and the insect attachment rate. Therefore, the directional mutagenesis method in Example 5 was adopted as a further preference in the present application.

The above are the preferred embodiments of the present application, which are not intended to limit the protection scope of the present application. Therefore, all equivalent changes made according to the structure, shape and principle of the present application should be covered within the protection scope of the present application.

What is claimed is:

1. A *Beauveria bassiana* strain with ultraviolet radiation resistance, wherein the *Beauveria bassiana* strain has an accession number of CGMCC No. 22466, wherein the *Beauveria bassiana* strain comprises ribosomal ribonucleic acid (rRNA) and a sequence of an rRNA gene of the *Beauveria bassiana* strain with ultraviolet radiation resistance is shown in SEQ ID NO 1.

2. An insecticidal preparation comprising the strain of claim 1.

* * * * *

SEQUENCE LISTING

```
Sequence total quantity: 1
SEQ ID NO: 1           moltype = DNA  length = 500
FEATURE                Location/Qualifiers
source                 1..500
                       mol_type = other DNA
                       organism = Beauveria bassiana
SEQUENCE: 1
acctacctat cgttgcttcg gcggactcgc cccagcccgg acgcggactg gaccagcggc  60
ccgccgggga cctcaaactc ttgtattcca gcatcttctg aatacgccgc aaggcaaaac  120
aaatgaatca aaactttcaa caacggatct cttggctctg gcatcgatga agaacgcagc  180
gaaacgcgat aagtaatgtg aattgcagaa tccagtgaat catcgaatct ttgaacgcac  240
attgcgcccg ccagcattct ggcgggcatg cctgttcgag cgtcatttca accctcgacc  300
tccccttggg gaggtcggcg ttggggaccg gcagcacacc gccggccctg aaatggagtg  360
gcggcccgtc cgcggcgacc tctgcgcagt aatacagctc gcaccggaac cccgacgcgg  420
ccacgccgta aaacacccaa cttctgaacg ttgacctcga atcaggtagg actacccgct  480
gaacttaagc atatcaataa                                              500
```